(12) United States Patent
Lange et al.

(10) Patent No.: US 7,745,476 B2
(45) Date of Patent: Jun. 29, 2010

(54) 1,3,5-TRISUBSTITUTED 4,5-DIHYDRO-1H-PYRAZOLE DERIVATIVES HAVING CB1-ANTAGONISTIC ACTIVITY

(75) Inventors: Josephus H. M. Lange, Weesp (NL); Cornelis G. Kruse, Weesp (NL); Herman H. Van Stuivenberg, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 1386 days.

(21) Appl. No.: 11/033,683

(22) Filed: Jan. 13, 2005

(65) Prior Publication Data

US 2005/0171179 A1 Aug. 4, 2005

Related U.S. Application Data

(60) Provisional application No. 60/539,983, filed on Jan. 30, 2004.

(51) Int. Cl.
*A61K 31/415* (2006.01)
*C07D 231/06* (2006.01)
(52) U.S. Cl. .................... 514/406; 548/379.4
(58) Field of Classification Search ............ 514/406; 548/379.4
See application file for complete search history.

(56) References Cited

U.S. PATENT DOCUMENTS

| 6,476,060 | B2 | 11/2002 | Lange et al. | |
|---|---|---|---|---|
| 2004/0248944 | A1 | 12/2004 | Kruse et al. | |
| 2006/0128673 | A1* | 6/2006 | Firnges et al. | 514/149 |
| 2006/0189658 | A1* | 8/2006 | Cuberes Altisen et al. | 514/326 |
| 2007/0015811 | A1* | 1/2007 | Cuberes | 514/406 |
| 2007/0073056 | A1* | 3/2007 | Torrens et al. | 540/575 |

FOREIGN PATENT DOCUMENTS

| DE | 3540934 A * 5/1987 |
|---|---|
| WO | WO 01/70700 A1 9/2001 |
| WO | WO 03/026647 A1 4/2003 |

OTHER PUBLICATIONS

International Search Report (PCT/EP2005/050339) dated May 6, 2005.
Meschler, J.P. et al. "Inverse Agonist Properties of N-(piperidin-1-yl)-5-(4-chlorophenyl)-1-(2, dichlorophenyl)-4-methyl-1H-pyrazole-3-carboxamide HCl(SR141716A) and 1-(2-chlorophenyl)-4-cyano-5-(4-methoxyphenyl)-1H-pyrazole-3-carboxylic acid phenylamide (CP-272871) for CB1 Cannabinoid Receptor," *Biochemical Pharmacology* 60(2000):1315-1323, Pergamon, Oxford, GB, XP002262541 ISSN: 0006-2952.

* cited by examiner

*Primary Examiner*—Kamal A Saeed
(74) *Attorney, Agent, or Firm*—Finnegan, Henderson, Farabow, Garrett & Dunner, L.L.P.

(57) ABSTRACT

The present invention relates to 1,3,5-trisubstituted 4,5-dihydro-1H-pyrazole derivatives as $CB_1$ antagonists, to methods for the preparation of these compounds and to novel intermediates useful for the synthesis of said pyrazole derivatives. The invention also relates to the use of a compound disclosed herein for the manufacture of a medicament giving a beneficial effect.

The compounds have the general formula (I)

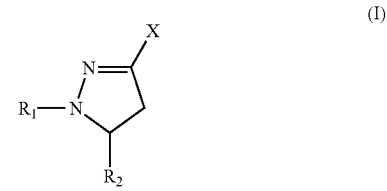

wherein the symbols have the meanings given in the specification.

17 Claims, No Drawings

1,3,5-TRISUBSTITUTED 4,5-DIHYDRO-1H-PYRAZOLE DERIVATIVES HAVING CB1-ANTAGONISTIC ACTIVITY

CROSS REFERENCE TO RELATED APPLICATION

This application claims the benefit of U.S. Provisional Application No. 60/539,983, filed Jan. 30, 2004, content of which is incorporated herein by reference.

The present invention relates to 1,3,5-trisubstituted 4,5-dihydro-1H-pyrazole derivatives as $CB_1$ antagonists, to methods for the preparation of these compounds and to novel intermediates useful for the synthesis of said pyrazole derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which cannabinoid receptors are involved, or that can be treated via manipulation of those receptors.

In WO 8805046, N-Aryl-4,5-dihydro-1H-pyrazole-3-carboxamide derivatives have been described as insecticides, but not as cannabinoid receptor antagonists. 3,4-Diaryl-4,5-dihydropyrazole-1-carboxamidine derivatives are known as $CB_1$ receptor antagonists (see WO 0170700, WO 0276949, WO 0326647 and WO 026648). However, the 4,5-dihydropyrazole derivatives described in this invention have a significantly different 1,3,5-substitution pattern and as a consequence have to be prepared via a entirely different synthetic route.

It has now surprisingly been found that potent and selective antagonism or inverse agonism of cannabinoid-$CB_1$ receptors is present in the novel 1,3,5-trisubstituted 4,5-dihydro-1H-pyrazole derivatives of the formula (I), tautomers thereof and salts thereof

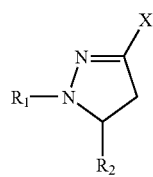

(I)

wherein:
$R_1$ and $R_2$ independently represent phenyl, thienyl or pyridyl which groups may be substituted with 1, 2 or 3 substituents Y, which can be the same or different, from the group branched or linear $C_{1-3}$-alkyl or alkoxy, phenyl, hydroxy, chloro; bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, or $R_1$ and/or $R_2$ represent naphtyl, X represents one of the subgroups (i) or (ii),

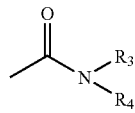

(i)

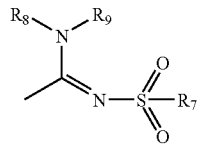

(ii)

wherein
$R_3$ represents a hydrogen atom or a branched or linear $C_{1-3}$ alkyl group,
$R_4$ represents a branched or linear $C_{1-8}$ alkyl or $C_{3-8}$-cycloalkyl-$C_{1-2}$-alkyl group, branched or linear $C_{1-8}$ alkoxy, $C_{3-8}$ cycloalkyl, $C_{5-10}$ bicycloalkyl, $C_{6-10}$ tricycloalkyl, which groups may contain one or more heteroatoms from the group (O, N, S) and which groups may be substituted with a hydroxy group, 1-3 methyl groups, an ethyl group or 1-3 fluoro atoms, or $R_4$ represents a phenyl, phenoxy, benzyl, phenethyl or phenylpropyl group, optionally substituted on their phenyl ring with 1-3 substituents Y, wherein Y has the abovementioned meaning, or $R_4$ represents a pyridyl or thienyl group, or $R_4$ represents a group $NR_5R_6$ wherein
$R_5$ and $R_6$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) and which heterocyclic group may be substituted with a branched or linear $C_{1-3}$ alkyl, phenyl, hydroxy or trifluoromethyl group or a fluoro atom, or
$R_3$ and $R_4$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) and which heterocyclic group may be substituted with a branched or linear $C_{1-3}$ alkyl, phenyl, amino, hydroxy or trifluoromethyl group or a fluoro atom,
$R_7$ represents a benzyl, phenyl, thienyl or pyridyl group, which groups may be substituted on their aromatic ring with 1, 2, 3 or 4 substituents Y, wherein Y has the meaning as indicated above, which can be the same or different, or $R_7$ represents $C_{1-8}$ branched or linear alkyl, $C_{3-8}$ alkenyl, $C_{3-10}$ cycloalkyl, $C_{5-10}$ bicycloalkyl, $C_{6-10}$ tricycloalkyl or $C_{5-8}$ cycloalkenyl or $R_7$ represents naphtyl or $R_7$ represents an amino group or $R_7$ represents a $C_{1-8}$ dialkylamino group, a $C_{1-8}$ monoalkylamino group or a saturated or unsaturated, monocyclic or bicyclic, heterocyclic group having 4 to 10 ring atoms, which heterocyclic group contains 1 or 2 nitrogen atoms and which heterocyclic group may contain 1 heteroatom from the group (O, S) and which heterocyclic group may be substituted with a branched or linear $C_{1-3}$ alkyl, phenyl, hydroxy or trifluoromethyl group or a fluoro atom,
$R_8$ represents a hydrogen atom or a branched or linear $C_{1-3}$ alkyl group,
$R_9$ represents a hydrogen atom or a branched or linear $C_{1-8}$ alkyl, $C_{3-8}$ cycloalkyl or $C_{2-10}$ heteroalkyl group which groups may be substituted with a keto group, trifluoromethyl group or a fluoro atom, or $R_9$ represents an amino, hydroxy, phenoxy or benzyloxy group or $R_9$ represents a branched or linear $C_{1-8}$ alkoxy group, which may be substituted with a hydroxy group, a trifluoromethyl group or a fluoro atom, or $R_9$ represents a phenyl, benzyl, pyridyl, thienyl, pyridylmethyl or phenethyl group wherein the aromatic rings may be substituted with 1, 2 or 3 of the substituents Y, wherein Y has the meaning as indicated above, or $R_9$ represents a group $NR_{10}R_{11}$ with the proviso that $R_8$ represents a hydrogen atom or a methyl group and wherein $R_{10}$ and $R_{11}$ are the same or different and represent $C_{1-4}$ alkyl or $C_{2-4}$ trifluoroalkyl or $R_{10}$ and $R_{11}$— together with the nitrogen atom to which they are bonded—form a saturated or unsaturated heterocyclic moiety having 4 to 8 ring atoms which heterocyclic moiety contains one or two atoms from the group (O, N, S) which saturated or unsaturated heterocyclic moiety may be substituted with a $C_{1-2}$ alkyl group or $R_8$ and $R_9$—together with the nitrogen atom to which they are bonded—form a saturated or unsaturated, monocyclic or bicyclic heterocyclic moiety having 4 to 10 ring atoms, which heterocyclic moiety contains one or two atoms from the group (O, N, S) or a keto group or —$SO_2$— group, which moiety may be substituted with a $C_{1-2}$ alkyl, hydroxy, phenyl, methylamino, dimethylamino, azetidinyl, pyrrolidinyl, piperidinyl or hexahydro-1H-azepinyl group.

At least one centre of chirality is present (at the $C_5$ position of the 4,5-dihydro-1H-pyrazole moiety) in the compounds of the formula (I). The invention relates both to racemates, mixtures of diastereomers and the individual stereoisomers of the compounds having formula (I). The invention also relates both to the E isomer, Z isomer and E/Z mixtures of compounds having formula (I).

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", *Expert Opin. Ther. Patents*, 14(3), 277-280, 2004; P. Ettmayer et al., "Lessons learned from marketed and investigational prodrugs", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxylmethylene derivative, an O-(acyloxymethylene carbamate) derivative, carbamate, ester, amide or enaminone.

The invention particularly relates to compounds having formula (I)

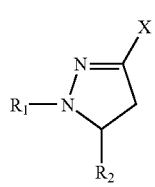

(I)

wherein $R_1$ and $R_2$ independently represent phenyl, which phenyl group may be substituted with 1, 2 or 3 substituents Y, which can be the same or different, from the group branched or linear $C_{1-3}$-alkyl or alkoxy, phenyl, hydroxy, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, or $R_1$ and/or $R_2$ represent naphtyl, thienyl or pyridyl, X represents one of the subgroups (i) or (ii),

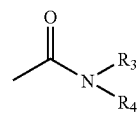

(i)

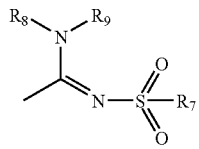

(ii)

wherein $R_3$ represents a hydrogen atom, $R_4$ represents a branched or linear $C_{1-8}$ alkyl, branched or linear $C_{1-8}$ alkoxy or $C_{3-8}$ cycloalkyl group, which groups may be substituted with a hydroxy group, 1-3 methyl groups, an ethyl group or 1-3 fluoro atoms, or $R_4$ represents a phenoxy, pyridyl or thienyl group, or $R_4$ represents a group $NR_5R_6$ wherein $R_5$ and $R_6$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) or $R_3$ and $R_4$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) and which heterocyclic group may be substituted with a methyl, hydroxy or trifluoromethyl group or a fluoro atom, $R_7$ represents a phenyl group, which phenyl group may be substituted on its aromatic ring with 1, 2, 3 or 4 substituents Y, wherein Y has the meaning as indicated above, which can be the same or different, or $R_7$ represents $C_{1-8}$ branched or linear alkyl, $C_{3-10}$ cycloalkyl or $C_{5-10}$ bicycloalkyl, or $R_7$ represents naphtyl or $R_7$ represents a amino group or $R_7$ represents a $C_{1-8}$ dialkylamino group, a $C_{1-8}$ monoalkylamino group or a saturated or unsaturated, monocyclic or bicyclic, heterocyclic group having 4 to 10 ring atoms, which heterocyclic group contains 1 or 2 nitrogen atoms and which heterocyclic group may contain 1 heteroatom from the group (O, S) and which heterocyclic group may be substituted with a branched or linear $C_{1-3}$ alkyl or hydroxy group, $R_8$ represent a hydrogen atom or a branched or linear $C_{1-3}$ alkyl group, $R_9$ represents a hydrogen atom or a branched or linear $C_{1-8}$ alkyl or $C_{3-8}$ cycloalkyl group which groups may be substituted with a trifluoromethyl group or a fluoro atom, or $R_9$ represents an amino, hydroxy, phenoxy or benzyloxy group or $R_9$ represents a branched or linear $C_{1-8}$ alkoxy group, or $R_9$ represents a phenyl group wherein the aromatic ring may be substituted with 1, 2 or 3 of the substituents Y, wherein Y has the meaning as indicated above, or $R_9$ represents a group $NR_{10}R_{11}$ with the proviso that $R_8$ represents a hydrogen atom or a methyl group and wherein $R_{10}$ and $R_{11}$ are the same or different and represent $C_{1-4}$ alkyl or $C_{2-4}$ trifluoroalkyl or $R_{10}$ and $R_{11}$—together with the nitrogen atom to which they are bonded—form a saturated or unsaturated heterocyclic moiety having 4 to 8 ring atoms which heterocyclic moiety contains one or two atoms from the group (O, N, S) or $R_8$ and $R_9$—together with the nitrogen atom to which they are bonded—form a saturated or unsaturated, monocyclic or bicyclic heterocyclic moiety having 4 to 10 ring atoms, which heterocyclic moiety contains one or two atoms from the group (O, N, S) or a keto group or —$SO_2$— group and tautomers, stereoisomers, prodrugs and salts thereof.

It was also found that compounds with the general formula (I) in which the meaning of $R_4$ is phenyl, i.e. compounds described in WO 8805046, are active as $CB_1$ receptor antagonists.

Due to the potent $CB_1$ antagonistic activity the compounds according to the invention are suitable for use in the treatment of psychiatric disorders such as psychosis, anxiety, depression, attention deficits, memory disorders, cognitive disorders, appetite disorders, obesity, in particular juvenile obesity and drug induced obesity, addiction, impulse control disorders, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea, cardiovascular disorders, atherosclerosis, liver cirrhosis and sexual disorders.

The cannabinoid receptor modulating activity of the compounds of the invention makes them particularly useful in the treatment of obesity, juvenile obesity and drug induced obesity, when used in combination with lipase inhibitors. Specific examples of compounds which can be used in such combination preparations are (but not restricted to) the synthetic lipase inhibitor orlistat, lipase inhibitors isolated from micro organisms such as lipstatin (from *Streptomyces toxytricini*), ebelactone B (from *Streptomyces aburaviensis*), synthetic derivatives of these compounds, as well as extracts of plants known to possess lipase inhibitory activity, for instance extracts of *Alpinia officinarum* or compounds isolated from such extracts like 3-methylethergalangin (from *A. officinarum*).

General Aspects of Syntheses

The synthesis of compounds having formula (I) wherein X represents subgroup (i) is outlined in Scheme 1. Intermediates having general formula (VII) can be obtained according to methods known, see for example: WO88/05046 and references cited therein. Intermediates having formula (V) can be obtained according to methods known, for example: Shawali et al., J. Heterocyclic Chem. 2003, 40 (2), 207 and references cited therein.

Diazotation of compounds having formula (II) can give a diazonium chloride of formula (III) by treatment with $NaNO_2$ under acidic conditions (HCl). Coupling of (III) with an alkyl 2-chloro-3-oxobutanoate derivative, such as ethyl 2-chloro-3-oxobutanoate (IV) can give a 2-chloro(hydrazono)acetate derivative of general formula (V). Reaction of (V) with an alkene derivative of formula (VI) can give a 1,5-disubstituted-4,5-dihydro-1H-pyrazole-3-carboxylate analogue of general formula (VII). A compound of general formula (VII) can react with an amine $R_3R_4NH$, preferably in the presence of trimethylaluminum ($Me_3Al$) to give a compound of formula (I), wherein X represents subgroup (i) and $R_3$ and $R_4$ have the meaning as given above on page 2. More information on trimethylaluminum $Al(CH_3)_3$ promoted amidation reactions of esters can be found in: J. I. Levin, E. Turos, S. M. Weinreb, Synth Commun. (1982), 12, 989-993.

Scheme 1

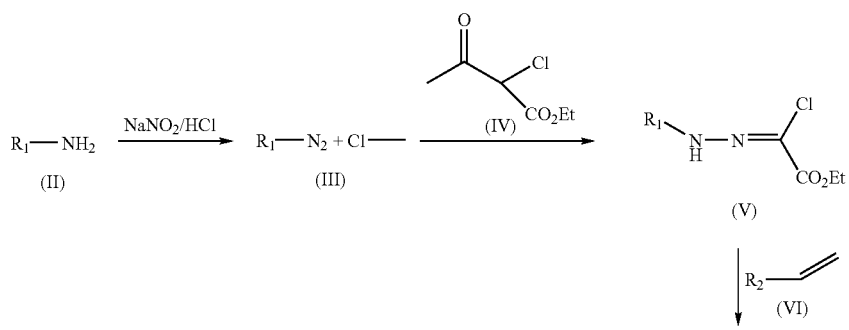

-continued

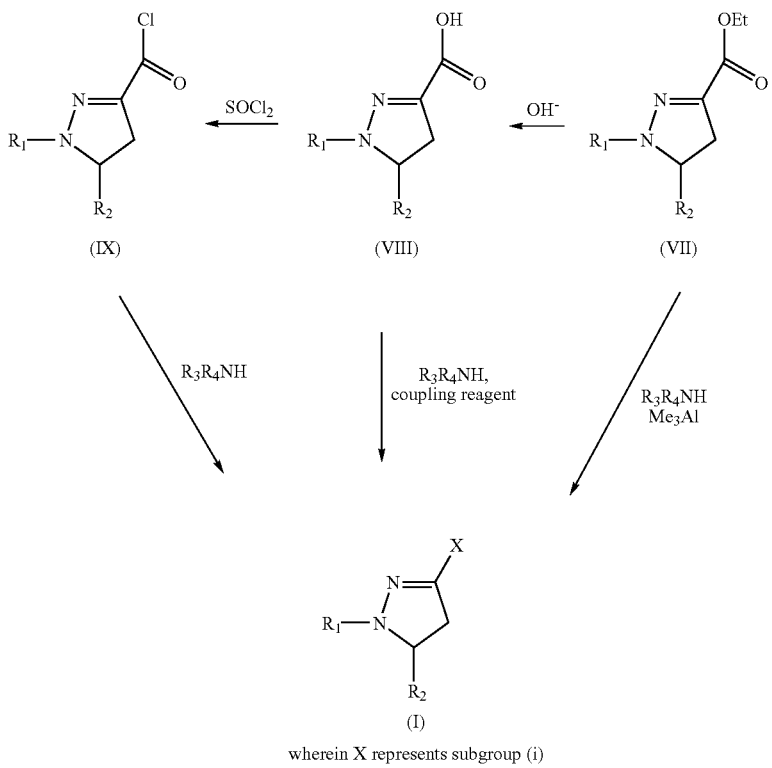

wherein X represents subgroup (i)

Alternatively, a compound of general formula (VII) can be hydrolysed to the corresponding carboxylic acid (VIII). The resulting carboxylic acid (VIII) can be reacted with an amine $R_3R_4NH$ to give a compound of formula (I), wherein X represents subgroup (i) and $R_3$ and $R_4$ have the meaning as given above on page 2, via activating and coupling methods such as formation of an active ester, or in the presence of a so-called coupling reagent, such as for example, DCC, HBTU, BOP, CIP (2-chloro-1,3-dimethylimidazolinium hexafluorophosphate), PyAOP (7-azabenzotriazol-1-yloxytris(pyrrolidino) phos-phonium hexafluorophosphate) and the like. More information on activating and coupling methods of amines to carboxylic acids can be found in:

a) M. Bodanszky and A. Bodanszky: *The Practice of Peptide Synthesis*, Springer-Verlag, New York, 1994; ISBN: 0-387-57505-7;
b) K. Akaji et al., *Tetrahedron Lett.* (1994), 35, 3315-3318);
c) F. Albericio et al., *Tetrahedron Lett.* (1997), 38, 4853-4856).

Alternatively, carboxylic acid (VIII) can be reacted with a halogenating agent such as thionyl chloride ($SOCl_2$) to give the corresponding carbonyl chloride (IX). Compound (IX) can be reacted with an amine $R_3R_4NH$ to give a compound of formula (I), wherein X represents subgroup (i) and $R_1$, $R_2$, $R_3$ and $R_4$ have the meaning as given above on page 2.

The synthesis of compounds having formula (I) wherein X represents subgroup (ii) is outlined in Scheme 2.

A compound of general formula (VII) can be converted to the corresponding carboxamidine derivative (X) for example by using trimethylaluminum ($Me_3Al$) and $NH_4Cl$, followed by a treatment with aqueous base. Information on such a conversion of an ester into a carboxamidine can be found in Tetrahedron. Lett. 2002, 43, 419 (Gielen et al.). Compounds of general formula (X) wherein $R_1$ and $R_2$ have the meaning as given above on page 2 are new. A compound of general formula (X) can be reacted with a sulfonyl chloride $R_7SO_2Cl$ in the presence of a base such as N-diisopropylethylamine (DIPEA) to give a compound of formula (I), wherein X represents subgroup (ii) and $R_1$, $R_2$, and $R_7$ have the meaning as given above on page 2, and $R_8$ and $R_9$ represent a hydrogen atom.

An intermediate of general formula $R_7SO_2NH_2$ can be prepared from the corresponding compound $R_7SO_2Cl$ or by synthetically related protocols (see for example; McManus et al., J. Med. Chem. 1965, 8, 766). A carbonyl chloride of general formula (IX) can be reacted with a compound of general formula $R_7SO_2NH_2$ in the presence of a base such as for example NaH to give a compound of general formula (XI) wherein $R_1$, $R_2$, and $R_7$ have the meaning as given above on pages 2 and 3. Compounds of general formula (XI) wherein $R_1$, $R_2$ and $R_7$ have the meaning as given above on pages 2 and 3 are new. The compound of formula (XI) can be reacted with a halogenating agent, for example a chlorinating agent such as $PCl_5$ and the like to give a compound of formula (XII), wherein Z represents a chloro or bromo atom. Compounds of general formula (XII) wherein $R_1$, $R_2$ and $R_7$ have the meaning as given above on page 2 are new. Compound (XII) can be reacted with an amine of general formula $R_8R_9NH$ to give a compound of general formula (I), wherein X represents subgroup (ii) and $R_1$, $R_2$, $R_7$, $R_8$ and $R_9$ have the meaning as given above on the pages 1-3.

Scheme 2

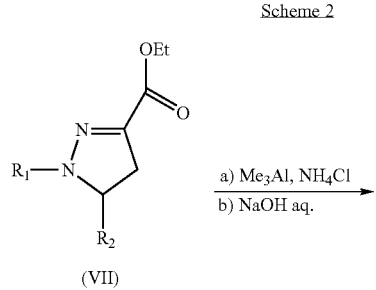

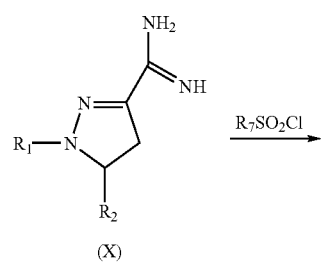

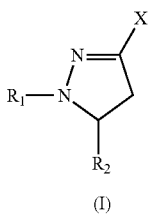

wherein X represents subgroup (ii), wherein $R_8$ and $R_9$ represent H

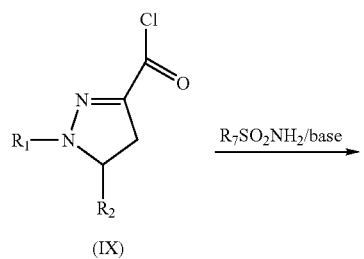

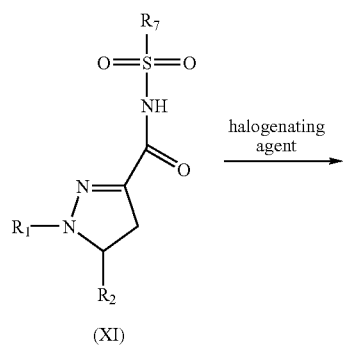

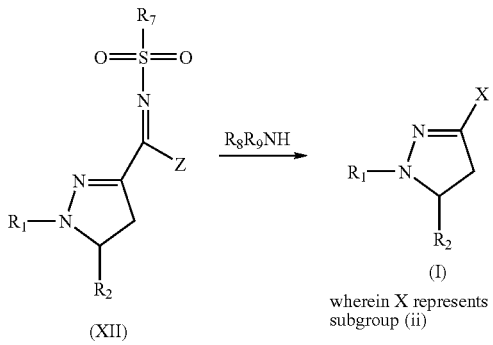

wherein X represents subgroup (ii)

The selection of the particular synthetic method depends on factors such as the compatibility of functional groups with the reagents used, the possibility to use protecting groups, catalysts, activating and coupling reagents and the ultimate structural features present in the final compound being prepared.

According to these procedures the following compounds can be prepared. They are intended to further illustrate the invention in more detail, and therefore are not deemed to restrict the scope of the invention in any way.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In Vitro Affinity for Cannabinoid-$CB_1$ Receptors

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In Vitro Cannabinoid-$CB_1$ Receptor Antagonism

In vitro $CB_1$ receptor antagonism can be assessed with the human $CB_1$ receptor cloned in Chinese hamster ovary (CHO) cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 ml DMEM, containing 0.2% bovine serum albumin (BSA). Stimulation of the $CB_1$ receptor by WIN 55,212-2 leads to activation of $PLA_2$ followed by release of [$^3$H]-arachidonic acid into the medium. This WIN 55,212-2-induced release is concentration-dependently antagonized by $CB_1$ receptor antagonists.

In Vivo Cannabinoid-$CB_1$ Receptor Antagonism

In vivo $CB_1$ antagonism can be assessed with the CP-55,940-induced hypotension test in rat. Male normotensive rats (225-300 g; Harlan, Horst, The Netherlands) are anaesthetized with pentobarbital (80 mg/kg ip). Blood pressure is measured, via a cannula inserted into the left carotid artery, by means of a Spectramed DTX-plus pressure transducer (Spectramed B.V., Bilthoven, The Netherlands). After amplification by a Nihon Kohden Carrier Amplifier (Type AP-621G; Nihon Kohden B.V., Amsterdam, The Netherlands), the blood pressure signal is registered on a personal computer (Compaq Deskpro 386s), by means of a Po-Ne-Mah data-acquisition program (Po-Ne-Mah Inc., Storrs, USA). Heart rate is derived from the pulsatile pressure signal. All compounds are administered orally as a microsuspension in 1% methylcellulose 30 minutes before induction of the anesthesia which is 60 minutes prior to administration of the $CB_1$ receptor agonist CP-55,940. The injection volume is 10 ml/kg. After haemodynamic stabilization the $CB_1$ receptor agonist CP-55,940 (0.1 mg/kg i.v.) is administered and the hypotensive effect established. (Wagner, J. A.; Jarai, Z.; Batkai, S.; Kunos, G. Hemodynamic effects of cannabinoids: coronary and cerebral vasodilation mediated by cannabinoid $CB_1$ receptors. *Eur. J. Pharmacol.* 2001, 423, 203-10).

Pharmaceutically acceptable salts may be obtained using standard procedures well known in the art, for example by mixing a compound of the present invention with a suitable acid, for instance an inorganic acid such as hydrochloric acid, or with an organic acid.

Dose

The affinity of the compounds of the invention for cannabinoid receptors was determined as described above. From the binding affinity measured for a given compound of formula (1), one can estimate a theoretical lowest effective dose. At a concentration of the compound equal to twice the measured $K_i$-value, 100% of the cannabinoid receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

EXAMPLES

Example 1

Syntheses of Specific Compounds

Compounds 1-4

Part A: To a stirred solution of 4-chloroaniline (15.68 gram, 0.123 mol) in ice (30 ml) and concentrated hydrochloric acid (30 ml) is slowly added a solution of $NaNO_2$ (9.0 gram, 0.13 mol) in water (16 ml) and the resulting solution is stirred for 1Hour at 0-5° C. and subsequently added to a cold mixture of NaOAc (32 gram, 0.39 mol), ethanol (520 ml) and ethyl 2-chloro-3-oxobutanoate (16.6 ml, 0.12 mol). After stirring the resulting mixture for 1 hour the formed precipitate is collected by filtration, washed with ethanol and dried in vacuo to give ethyl 2-chloro[(4-chlorophenyl)hydrazono]acetate (22.99 gram, 73% yield). Melting point: 147.5-149.5° C. $^1$H-NMR (200 MHz, $CDCl_3$): δ1.40 (t, J=7 Hz, 3H), 4.39 (q, J=7 Hz, 2H), 7.16 (br d, J=8 Hz, 2H), 7.30 (br d, J=8 Hz, 2H), 8.31 (br s, 1H).

Part B: To a stirred boiling solution of ethyl 2-chloro[(4-chlorophenyl) hydrazono]acetate (22.95 gram, 0.088 mol) and styrene (30.3 ml, 0.264 mol) in benzene (140 ml) is added triethylamine (34.3 ml, 0.247 mol) and the resulting solution is heated at reflux temperature for 1 hour. The resulting solution is cooled to room temperature and the formed precipitate is removed by filtration and washed with toluene. The filtrate is concentrated in vacuo and purified by flash chromatography (silica gel, dichloromethane) to give ethyl 1-(4-chlorophenyl)-5-phenyl-4,5-dihydro-(1H)-pyrazole-3-carboxylate (27.2 gram, 94% yield) as a syrup which slowly solidifies on standing. $^1$H-NMR (200 MHz, $CDCl_3$): δ1.38 (t, J=7 Hz, 3H), 3.06 (dd, J=18 and 7 Hz, 1H), 3.73 (dd, J=18 and 13 Hz, 1H), 4.33 (q, J=7 Hz, 2H), 5.38 (dd, J=13 and 7 Hz, 1H), 7.02 (br d, J=8 Hz, 2H), 7.08-7.40 (m, 7H).

Part C: To a stirred suspension of ethyl 1-(4-chlorophenyl)-5-phenyl-4,5-dihydro-(1H)-pyrazole-3-carboxylate (23.0 gram, 0.07 mol) in methanol (200 ml) is added water (15 ml) and concentrated NaOH (10 ml) and the resulting solution is heated at reflux temperature for 2 hours. The methanol is partly removed by evaporation and the residue is dissolved in a mixture of water and ethyl acetate. Ice, concentrated HCl (20 ml) and ethyl acetate are successively added, the ethyl acetate layer collected, dried over $MgSO_4$, filtered and concentrated in vacuo. The resulting residue is washed with diethyl ether (100 ml) and diisopropyl ether respectively, to give 1-(4-chlorophenyl)-5-phenyl-4,5-dihydro-(1H)-pyrazole-3-carboxylic acid (16.46 gram, 78% yield). Melting point: 177-179° C.

Part D: To a stirred suspension of 1-(4-chlorophenyl)-5-phenyl-4,5-dihydro-(1H)-pyrazole-3-carboxylic acid (1.50 gram, 5 mmol) in anhydrous acetonitrile (40 ml) is successively added N-diisopropylethylamine (DIPEA) (1.92 ml, 11 mmol), O-benzotriazol-1-yl-N,N, N',N'-tetramethyluronium hexafluorophosphate (HBTU) (2.08 g, 5.5 mmol) and 1-aminopiperidine (0.59 ml, 5.5 mmol) and the resulting mixture is reacted at room temperature for 16 hours in a $N_2$ atmosphere. The mixture is concentrated and added to a mixture of ethyl acetate and aqueous $NaHCO_3$. The Ethyl acetate layer is collected, dried over MgSO₄, filtered and concentrated in vacuo. The resulting residue is recrystallised from acetonitrile to give N-(piperidin-1-yl)-1-(4-chlorophenyl)-5-phenyl-4,5-dihydro-(1H)-pyrazole-3-carboxamide (compound 1), 1.34 gram, 70% yield). Melting point: 189-192° C.

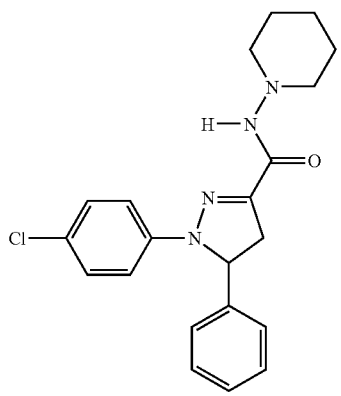

compound 1

In an analogous manner the compounds having formula (I) listed below have been prepared, the compounds 2, 3 and 4:

Compound 2: N-(Piperidin-1-yl)-5-(4-chlorophenyl)-1-(2,4-dichlorophenyl)-4,5-dihydro-(1H)-pyrazole-3-carboxamide. Melting point: 185-187° C.

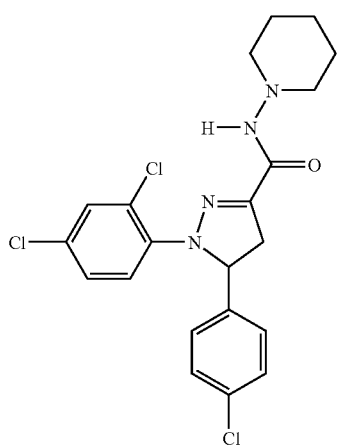

compound 2

Compound 3: N-(Piperidin-1-yl)-1-(2,4-dichlorophenyl)-5-phenyl-4,5-dihydro-(1H)-pyrazole-3-carboxamide. Melting point: 163-165° C.

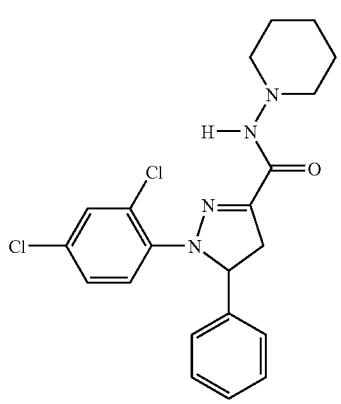

compound 3

Compound 4: N-Cyclohexyl)-1-(2,4-dichlorophenyl)-5-phenyl-4,5-dihydro-(1H)-pyrazole-3-carboxamide. Melting point: 160-163.5° C.

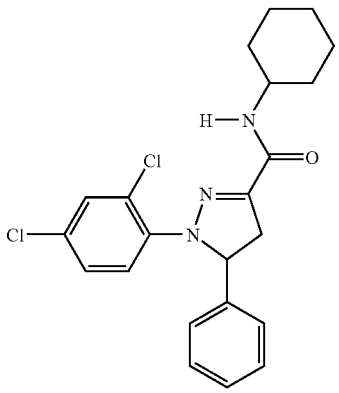

compound 4

Compounds 5 and 6

Part A: A stirred suspension of NH₄Cl (2.68 g, 0.05 mol) in toluene (25 ml) is cooled to 0° C. in an N₂ atmosphere. A solution of Me₃Al in toluene (25 ml of a 2 M solution) is slowly added and the mixture is allowed to attain room temperature. A solution of ethyl 1-(4-chlorophenyl)-5-phenyl-4,5-dihydro-(1H)-pyrazole-3-carboxylate (3.29 gram, 10 mmol) in toluene (25 ml) is slowly added and the reaction mixture is stirred at 80° C. for 16 hours. After cooling to 0° C. methanol is slowly added and the formed precipitate is removed by filtration. The filtrate is concentrated and the residue is dissolved in a mixture of dichloromethane and methanol. The formed precipitate is removed by filtration. The filtrate is concentrated and the remaining residue crystallised from dichloromethane to give 1-(4-chlorophenyl)-5-phenyl-4,5-dihydro-(1H)-pyrazole-3-carboxamidine.HCl (2.70 g, 73% yield). ¹H-NMR (200 MHz, DMSO-d₆): δ3.08 (dd, J=18 and 7 Hz, 1H), 3.82 (dd, J=18 and 13 Hz, 1H), 5.84 (dd, J=13 and 7 Hz, 1H), 7.15-7.46 (m, 9H), 8.85 (br s, 2H), 9.00 (br s, 2H).

Analogously was prepared 1-(2,4-dichlorophenyl)-5-phenyl-4,5-dihydro-(1H)-pyrazole-3-carboxamidine.HCl.
¹H-NMR (200 MHz, DMSO-d₆ with addition of some trifluoroacetic acid): δ3.32 (dd, J=18 and 7 Hz, 1H), 3.82 (dd, J=18 and 13 Hz, 1H), 6.08 (dd, J=13 and 7 Hz, 1H), 7.13-7.31 (m, 6H), 7.42 (d, J=2 Hz, 1H), 7.52 (d, J=8 Hz, 1H), 8.95 (br s, 2H), 9.05 (br s, 2H).

Part B: To a stirred solution of 1-(4-chlorophenyl)-5-phenyl-4,5-dihydro-(1H)-pyrazole-3-carboxamidine.HCl (1.87 gram, 5 mmol) and 4-fluorophenylsulfonyl chloride (0.97 g, 5 mmol) in anhydrous acetonitrile (20 ml) is added triethylamine (2.1 ml, 15 mmol) and the resulting mixture is stirred at room temperature for 16 hours. After concentration in vacuo, the residue is dissolved in a mixture of Ethyl acetate and water. The Ethyl acetate layer is collected, dried over MgSO₄, filtered and concentrated in vacuo. The resulting residue is recrystallised from methyl-t-butyl ether to give N-[(4-fluorophenyl)sulfonyl]-1-(4-chlorophenyl)-5-phenyl-4,5-dihydro-(1H)-pyrazole-3-carboxamidine (1.22 gram, 54% yield). Melting point: 200-203.5° C.

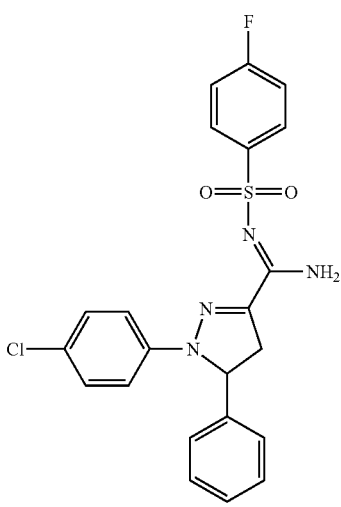

compound 5

In an analogous manner compound 6 was prepared:

Compound 6: N-[(4-fluorophenyl)sulfonyl]-1-(2,4-dichlorophenyl)-5-phenyl-4,5-dihydro-(1H)-pyrazole-3-carboxamidine. Melting point: 167-169.5° C.

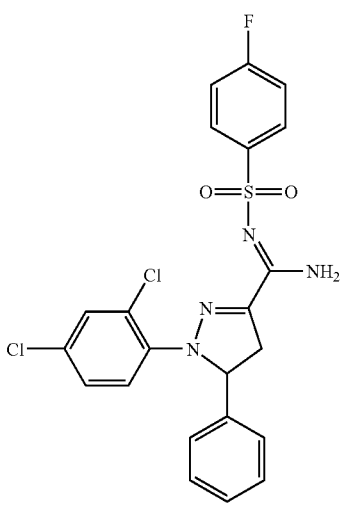

compound 6

Compounds 7-9

Part A: To a stirred solution of 1-(4-chlorophenyl)-5-phenyl-4,5-dihydro-(1H)-pyrazole-3-carboxylic acid (3.01 gram, 10 mmol) in toluene (30 ml) is added thionyl chloride (SOCl$_2$) (2.9 ml, 40 mmol) and the resulting mixture is heated at 80° C. for 1 hour. After thorough concentration in vacuo the residue is dissolved in anhydrous acetonitrile (50 ml) to give solution A. To a stirred solution 4-chlorophenylsulfonamide (1.92 gram, 10 mmol) in acetonitrile (50 ml) is added concentrated NaOH (1.3 ml, 25 mmol). To the resulting mixture is slowly added solution A. The resulting mixture is stirred at room temperature for 16 hours. Hydrochloric acid (50 ml of a 1N solution) and water (50 ml) are added. The precipitate was collected by filtration, washed with water, dissolved in dichloromethane, dried over MgSO$_4$, filtered and concentrated in vacuo. The resulting residue is recrystallised from ethanol to give N-[(4-chlorophenyl)sulfonyl]-1-(4-chlorophenyl)-5-phenyl-4,5-dihydro-(1H)-pyrazole-3-carboxamide (4.25 gram, 79% yield). Melting point: 226-229° C.

Analogously were prepared N-[(4-chlorophenyl)sulfonyl]-1-(2,4-dichlorophenyl)-5-phenyl-4,5-dihydro-(1H)-pyrazole-3-carboxamide (melting point: 178-181° C.) and N-{[4-(trifluoromethyl)phenyl]sulfonyl}-1-(2,4-dichlorophenyl)-5-phenyl-4,5-dihydro-(1H)-pyrazole-3-carboxamide (melting point: 175-177° C.).

Part B: A stirred mixture of N-[(4-chlorophenyl)sulfonyl]-1-(4-chlorophenyl)-5-phenyl-4,5-dihydro-(1H)-pyrazole-3-carboxamide (2.36 gram, 5 mmol), PCl$_5$ (1.15 g, 5.5 mmol) and chlorobenzene (50 ml) is heated for 90 minutes at 140° C. After cooling the mixture to room temperature the residue is dissolved in dichloromethane and methylamine.HCl (0.34 g, 5 mmol) and DIPEA (1.74 ml, 10 mmol) are successively added. The resulting mixture is stirred for 16 hours at room temperature, twice washed with water, dried over MgSO$_4$, filtered and concentrated in vacuo. The resulting residue is further purified by flash chromatography (silica gel, dichloromethane/acetone=99/1 (v/v/), followed by crystallization from diisopropyl ether to give N-[(4-chlorophenyl)sulfonyl]-N'-methyl-1-(4-chlorophenyl)-5-phenyl-4,5-dihydro-(1H)-pyrazole-3-carboxamidine (0.36 gram, 15% yield). Melting point: 134-144° C. R$_f$ (silica gel, diethyl ether=0.4).

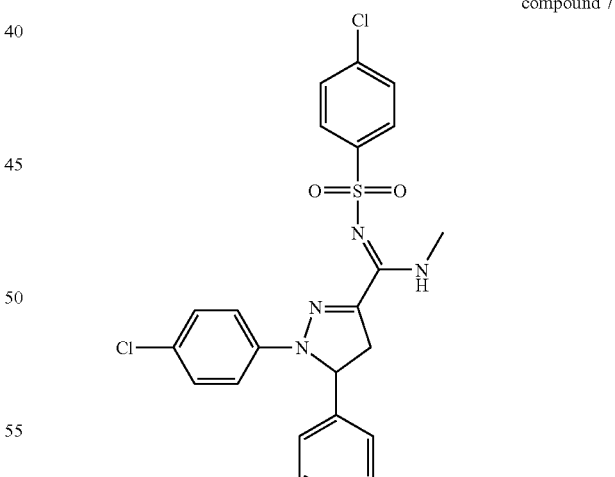

compound 7

In an analogous manner the compounds having formula (I) listed below have been prepared:

Compound 8: N-[(4-Chlorophenyl)sulfonyl]-N'-methyl-1-(2,4-dichlorophenyl)-5-phenyl-4,5-dihydro-(1H)-pyrazole-3-carboxamidine. Melting point: 128-130.5° C. R$_f$(silica gel, diethyl ether=0.4).

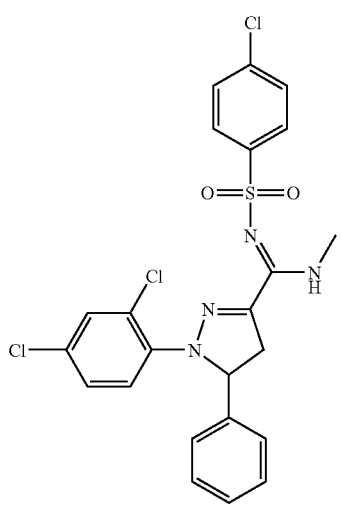

compound 8

Compound 9: N-{[(4-Trifluoromethyl)phenyl]sulfonyl}-N'-methyl-1-(2,4-dichlorophenyl)-5-phenyl-4,5-dihydro-(1H)-pyrazole-3-carboxamidine. Melting point: 157-159° C. $R_f$ (silica gel, diethyl ether=0.5).

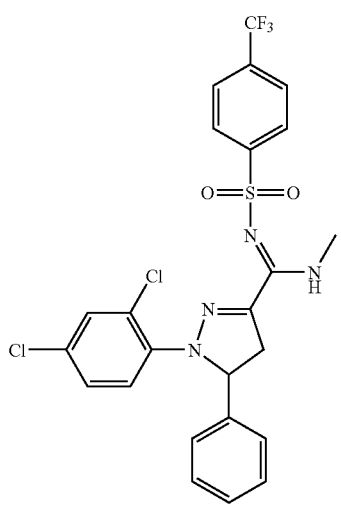

compound 9

Compounds 10 and 11

Part A: To a stirred solution of 1-(4-chlorophenyl)-5-phenyl-4,5-dihydro-(1H)-pyrazole-3-carboxylic acid (3.01 gram, 10 mmol) in toluene (30 ml) is added thionyl chloride (SOCl$_2$) (2.9 ml, 40 mmol) and the resulting mixture is heated at 80° C. for 1 hour. After thorough concentration in vacuo the residue is dissolved in anhydrous acetonitrile (50 ml) to give solution B. To a ice-cooled stirred solution of piperidine-1-sulfonamide (3.28 gram, 20 mmol) in anhydrous acetonitrile (50 ml) is added NaH (60% dispersion, 0.80 g, 20 mmol) and the resulting mixture is stirred at room temperature for 1 hour. To the resulting suspension is slowly added solution B. The resulting mixture is stirred at room temperature for 16 hours and subsequently concentrated in vacuo. Hydrochloric acid (1N solution) and dichloromethane are added to the residue. The dichloromethane layer is collected, washed with water, dried over MgSO$_4$, filtered and concentrated in vacuo. The resulting residue is recrystallised from ethanol to give N-[(piperidin-1-yl)sulfonyl]-1-(4-chlorophenyl)-5-phenyl-4,5-dihydro-(1H)-pyrazole-3-carboxamide (3.68 gram, 82% yield). Melting point: 239.5-241.5° C.

Analogously was prepared N-[(morpholin-4-yl)sulfonyl]-1-(2,4-dichlorophenyl)-5-phenyl-4,5-dihydro-(1H)-pyrazole-3-carboxamide. Melting point: 176-179° C.

Part B: A stirred mixture of N-[(piperidin-1-yl)sulfonyl]-1-(4-chlorophenyl)-5-phenyl-4,5-dihydro-(1H)-pyrazole-3-carboxamide (2.23 gram, 5 mmol), PCl$_5$ (1.15 g, 5.5 mmol) and chlorobenzene (50 ml) is heated for 90 minutes at 140° C. After cooling the mixture to room temperature, followed by concentration in vacuo, the residue is dissolved in dichloromethane and methylamine.HCl (0.34 g, 5 mmol) and DIPEA (1.74 ml, 10 mmol) are successively added. The resulting mixture is stirred for 1 hour at room temperature, twice washed with water, dried over MgSO$_4$, filtered and concentrated in vacuo. The resulting residue is further purified by flash chromatography (silica gel, dichloromethane), followed by crystallization from diisopropyl ether to give N-[(piperidin-1-yl)sulfonyl]-N'-methyl-1-(4-chlorophenyl)-5-phenyl-4,5-dihydro-(1H)-pyrazole-3-carboxamidine (1.12 gram, 49% yield). Melting point: 141-144° C. $R_f$ (silica gel, diethyl ether=0.2).

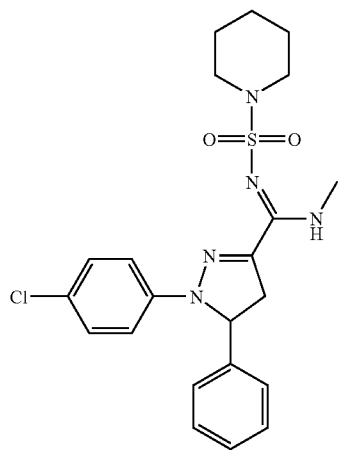

compound 10

In an analogous manner the compounds having formula (I) listed below have been prepared:

Compound 11: N-[(Morpholin-4-yl)sulfonyl]-N'-methyl-1-(2,4-dichlorophenyl)-5-phenyl-4,5-dihydro-(1H)-pyrazole-3-carboxamidine. Melting point: 161-165° C. $R_f$ (silica gel, dichloromethane/acetone=98/2 (v/v)=0.15).

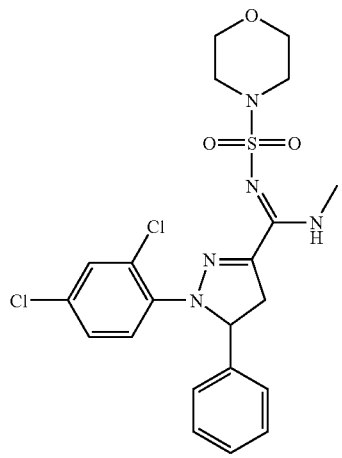

compound 11

Example 2

Formulations Used in Animal Studies

For oral (p.o.) administration: to the desired quantity (0.5-5 mg) of the solid compound 3 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 3 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 3

Pharmacological Test Results

Cannabinoid receptor affinity and functional in vitro data obtained according to the protocols given above are shown in the table below.

TABLE 1 pharmacological data

| | Human cannabinoid-$CB_1$ receptor | |
|---|---|---|
| Compound nr | In vitro affinity $pK_i$ value | In vitro antagonism % inhibition at $10^{-6}$M |
| Compound 3 | 7.6 | 98% |
| Compound 10 | 7.1 | 79% |

The invention claimed is:

1. A compound of formula (1), a tautomer, a stereoisomer, or an N-oxide thereof, or a salt or a hydrate of any of the foregoing:

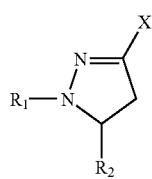

(I)

wherein:
  $R_1$ and $R_2$, which may be identical or different, are each chosen from
    phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and
    naphthyl;
  X is chosen from (i) and (ii),

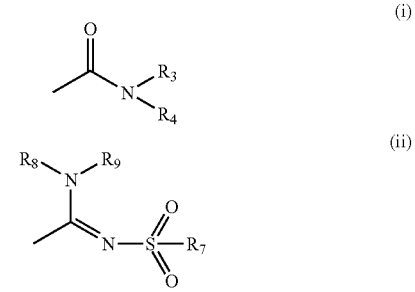

wherein:
  $R_3$ is chosen from hydrogen atoms and branched or linear $C_{1-3}$ alkyl groups;
  $R_4$ is chosen from
    branched or linear $C_{1-8}$ alkyls and $C_{3-8}$-cycloalkyl-$C_{1-2}$-alkyl groups, branched or linear $C_{1-8}$ alkoxys, $C_{3-8}$ cycloalkyls, $C_{5-10}$ bicycloalkyls, $C_{6-10}$ tricycloalkyls, optionally comprising at least one heteroatom chosen from O, N, and S and optionally substituted with a group chosen from hydroxy groups, from 1 to 3 methyl groups, ethyl groups, and from 1 to 3 fluoro atoms,
    phenoxy, benzyl, phenethyl and phenylpropyl groups, optionally substituted on the phenyl ring with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl,
    pyridyl and thienyl groups, and
    $NR_5R_6$ wherein:
      $R_5$ and $R_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms; or
  $R_3$ and $R_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms;
  $R_7$ is chosen from
    benzyl, phenyl, thienyl and pyridyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$ dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms;

$R_8$ is chosen from hydrogen atoms and branched or linear $C_{1-3}$ alkyls;

$R_9$ is chosen from hydrogen atoms and branched or linear $C_{1-8}$ alkyls, $C_{3-8}$ cycloalkyls and $C_{2-10}$ heteroalkyls, optionally substituted with a group chosen from keto groups, trifluoromethyl groups and fluoro atoms, amino, hydroxy, phenoxy and benzyloxy groups branched or linear $C_{1-8}$ alkoxy groups, optionally substituted with an entity chosen from hydroxy groups, trifluoromethyl groups and fluoro atoms, phenyl, benzyl, pyridyl, thienyl, pyridylmethyl and phenethyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S, and the heterocyclic group is optionally substituted with $C_{1-2}$ alkyl groups; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —$SO_2$— groups, wherein the heterocyclic group is optionally substituted with $C_{1-2}$ alkyls, hydroxys, phenyls, methylaminos, dimethylaminos, azetidinyls, pyrrolidinyls, piperidinyls and hexahydro-1H-azepinyls.

2. The compound according to claim 1, wherein:

$R_1$ and $R_2$, which may be identical or different, are each chosen from phenyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

$R_3$ comprises a hydrogen atom;

$R_4$ is chosen from branched or linear $C_{1-8}$ alkyls, branched or linear $C_{1-8}$ alkoxys, and $C_{3-8}$ cycloalkyls, optionally substituted with at least one group chosen from hydroxy groups, from 1 to 3 methyl groups, an ethyl group, and from 1 to 3 fluoro atoms, phenoxy, -pyridyl and thienyl groups, and $NR_5R_6$ wherein:

$R_5$ and $R_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S; or $R_3$ and $R_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from methyl groups, hydroxy groups, trifluoromethyl groups and fluoro atoms $R_7$ is chosen from phenyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-10}$ cycloalkyls, and $C_{5-10}$ bicycloalkyls, naphthyl, amino groups, and $C_{1-8}$ dialkylamino groups, $C_{1-8}$ monoalkylamino groups and saturated or unsaturated, monocyclic or bicyclic, heterocyclic groups having from 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with branched or linear $C_{1-3}$ alkyls and hydroxys;

$R_8$ is chosen from hydrogen atoms and branched or linear $C_{1-3}$ alkyls;

$R_9$ is chosen from hydrogen atoms and branched or linear $C_{1-4}$ alkyls or $C_{3-8}$ cycloalkyls, optionally substituted with a group chosen from trifluoromethyl groups and fluoro atoms, amino, hydroxy, phenoxy and benzyloxy groups, branched or linear $C_{1-8}$ alkoxy groups, phenyl groups, wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or R$_{10}$ and R$_{11}$, together with the nitrogen atom to which they are bonded, form a saturated or unsaturated heterocyclic group comprising from 4 to 8 ring atoms wherein the heterocyclic group comprises one or two atoms chosen from O, N, and S; or R$_8$ and R$_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —SO$_2$— groups.

3. The compound according to claim 1, wherein the formula (1) compound is chosen from:

N-(piperidin-1-yl)-1-(4-chlorophenyl)-5-phenyl-4,5-dihydro-(1H)-pyrazole-3-carboxamide, N-(Piperidin-1-yl)-5-(4-chlorophenyl)-1-(2,4-dichlorophenyl)-4,5-dihydro-(1H)-pyrazole-3-carboxamide, N-(Piperidin-1-yl)-1-(2,4-dichlorophenyl)-5-phenyl-4,5-dihydro-(1H)-pyrazole-3-carboxamide, N-(Cyclohexyl)-1-(2,4-dichlorophenyl)-5-phenyl-4,5-dihydro-(1H)-pyrazole-3-carboxamide, N-[(4-fluorophenyl)sulfonyl]-1-(4-chlorophenyl)-5-phenyl-4,5-dihydro-(1H)-pyrazole-3-carboxamidine, N-[(4-fluorophenyl)sulfonyl]-1-(2,4-dichlorophenyl)-5-phenyl-4,5-dihydro-(1H)-pyrazole-3-carboxamidine, N-[(4-chlorophenyl)sulfonyl]-N'-methyl-1-(4-chlorophenyl)-5-phenyl-4,5-dihydro-(1H)-pyrazole-3-carboxamidine, N-[(4-Chlorophenyl)sulfonyl]-N'-methyl-1-(2,4-dichlorophenyl)-5-phenyl-4,5-dihydro-(1H)-pyrazole-3-carboxamidine, N-{[(4-Trifluoromethyl)phenyl]sulfonyl}-N'-methyl-1-(2, 4-dichlorophenyl)-5-phenyl-4,5-dihydro-(1H)-pyrazole-3-carboxamidine, N-[(piperidin-1-yl)sulfonyl]-N'-methyl-1-(4-chlorophenyl)-5-phenyl-4,5-dihydro-(1H)-pyrazole-3-carboxamidine, and N-[(Morpholin-4-yl)sulfonyl]-N'-methyl-1-(2,4-dichlorophenyl)-5-phenyl-4,5-dihydro-(1H)-pyrazole-3-carboxamidine.

4. A pharmaceutical composition comprising:

at least one pharmaceutically acceptable carrier, at least one pharmaceutically acceptable auxiliary substance or a combination thereof, and an effective amount of at least one compound of formula (1), a tautomer, a stereoisomer, or an N-oxide thereof, or a salt or a hydrate of any of the foregoing:

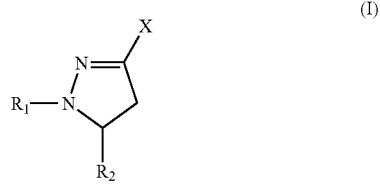

(I)

wherein:

R$_1$ and R$_2$, which may be identical or different, are each chosen from phenyls, thienyls and pyridyls, optionally substituted with 1, 2 or 3 substituents Y, which may be identical or different, chosen from branched or linear C$_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

X is chosen from (i) and (ii),

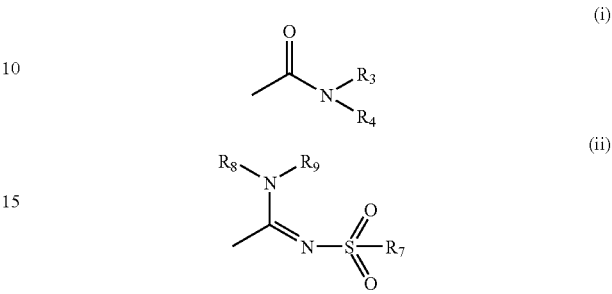

wherein:

R$_3$ is chosen from hydrogen atoms and branched or linear C$_{1-3}$ alkyl groups;

R$_4$ is chosen from branched or linear C$_{1-8}$ alkyls and C$_{3-8}$-cycloalkyl-C$_{1-2}$-alkyl groups, branched or linear C$_{1-8}$ alkoxys, C$_{3-8}$ cycloalkyls, C$_{5-10}$ bicycloalkyls, C$_{6-10}$ tricycloalkyls, optionally comprising at least one heteroatom chosen from O, N, and S and optionally substituted with a group chosen from hydroxy groups, from 1 to 3 methyl groups, ethyl groups, and from 1 to 3 fluoro atoms, phenoxy, benzyl, phenethyl and phenylpropyl groups, optionally substituted on the phenyl ring with 1, 2 or 3 substituents Y, which may be identical or different, chosen from branched or linear C$_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, pyridyl and thienyl groups, and NR$_5$R$_6$ wherein:

R$_5$ and R$_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear C$_{1-3}$ alkyls, phenyls, hydroxy, trifluoromethyl groups and fluoro atoms; or R$_3$ and R$_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear C$_{1-3}$ alkyls, phenyls, hydroxy, trifluoromethyl groups and fluoro atoms R$_7$ is chosen from benzyl, phenyl, thienyl and pyridyl groups, optionally substituted on the aromatic ring with 1, 2, 3 or 4 substituents Y, which may be identical or different, chosen from branched or linear C$_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl, and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$ dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms;

$R_8$ is chosen from hydrogen atoms and branched or linear $C_{1-3}$ alkyls;

$R_9$ is chosen from hydrogen atoms and branched or linear $C_{1-8}$ alkyls, $C_{3-8}$ cycloalkyls and $C_{2-10}$ heteroalkyls, optionally substituted with a group chosen from keto groups, trifluoromethyl groups and fluoro atoms, amino, hydroxy, phenoxy and benzyloxy groups branched or linear $C_{1-8}$ alkoxy groups, optionally substituted with an entity chosen from hydroxy groups, trifluoromethyl groups and fluoro atoms, phenyl, benzyl, pyridyl, thienyl, pyridylmethyl and phenethyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S, and the heterocyclic group is optionally substituted with $C_{1-2}$ alkyl groups; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —$SO_2$— groups, wherein the heterocyclic group is optionally substituted with $C_{1-2}$ alkyls, hydroxys, phenyls, methylaminos, dimethylaminos, azetidinyls, pyrrolidinyls, piperidinyls and hexahydro-1H-azepinyls.

5. The pharmaceutical composition of claim 4, wherein:

$R_1$ and $R_2$, which may be identical or different, are each chosen from phenyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

$R_3$ comprises a hydrogen atom;

$R_4$ is chosen from branched or linear $C_{1-8}$ alkyls, branched or linear $C_{1-8}$ alkoxys, and $C_{3-8}$ cycloalkyls, optionally substituted with at least one group chosen from hydroxy groups, from 1 to 3 methyl groups, an ethyl group, and from 1 to 3 fluoro atoms, phenoxy, -pyridyl and thienyl groups, and $NR_5R_6$ wherein:

$R_5$ and $R_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S; or $R_3$ and $R_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from methyl groups, hydroxy groups, trifluoromethyl groups and fluoro atoms $R_7$ is chosen from phenyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-10}$ cycloalkyls, and $C_{5-10}$ bicycloalkyls, naphthyl, amino groups, and $C_{1-8}$ dialkylamino groups, $C_{1-8}$ monoalkylamino groups and saturated or unsaturated, monocyclic or bicyclic, heterocyclic groups having from 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with branched or linear $C_{1-3}$ alkyls and hydroxys;

$R_8$ is chosen from hydrogen atoms and branched or linear $C_{1-3}$ alkyls;

$R_9$ is chosen from hydrogen atoms and branched or linear $C_{1-4}$ alkyls or $C_{3-8}$ cycloalkyls, optionally substituted with a group chosen from trifluoromethyl groups and fluoro atoms, amino, hydroxy, phenoxy and benzyloxy groups, branched or linear $C_{1-8}$ alkoxy groups, phenyl groups, wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —$SO_2$— groups.

6. The pharmaceutical composition of claim 4, wherein the formula (1) compound is chosen from N-(piperidin-1-yl)-1-(4-chlorophenyl)-5-phenyl-4,5-dihydro-(1H)-pyrazole-3-carboxamide, N-(Piperidin-1-yl)-5-(4-chlorophenyl)-1-(2,4-dichlorophenyl)-4,5-dihydro-(1H)-pyrazole-3-carboxamide, N-(Piperidin-1-yl)-1-(2,4-dichlorophenyl)-5-phenyl-4,5-dihydro-(1H)-pyrazole-3-carboxamide, N-(Cyclohexyl)-1-(2,4-dichlorophenyl)-5-phenyl-4,5-dihydro-(1H)-pyrazole-3-carboxamide, N-[(4-fluorophenyl)sulfonyl]-1-(4-chlorophenyl)-5-phenyl-4,5-dihydro-(1H)-pyrazole-3-carboxamidine, N-[(4-fluorophenyl)sulfonyl]-1-(2,4-dichlorophenyl)-5-phenyl-4,5-dihydro-(1H)-pyrazole-3-carboxamidine, N-[(4-chlorophenyl)sulfonyl]-N'-methyl-1-(4-chlorophenyl)-5-phenyl-4,5-dihydro-(1H)-pyrazole-3-carboxamidine, N-[(4-Chlorophenyl)sulfonyl]-N'-methyl-1-(2,4-dichlorophenyl)-5-phenyl-4,5-dihydro-(1H)-pyrazole-3-carboxamidine, N-{[(4-Trifluoromethyl)phenyl]sulfonyl}-N'-methyl-1-(2,4-dichlorophenyl)-5-phenyl-4,5-dihydro-(1H)-pyrazole-3-carboxamidine, N-[(piperidin-1-yl)sulfonyl]-N'-methyl-1-(4-chlorophenyl)-5-phenyl-4,5-dihydro-(1H)-pyrazole-3-carboxamidine, and N-[(Morpholin-4-yl)sulfonyl]-N'-methyl-1-(2,4-dichlorophenyl)-5-phenyl-4,5-dihydro-(1H)-pyrazole-3-carboxamidine.

7. A compound of formula (X), a tautomer thereof, or a salt thereof of any of the foregoing:

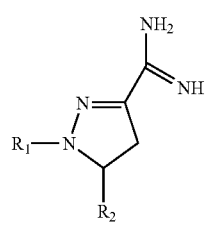

(X)

wherein $R_1$ and $R_2$, which may be identical or different, are each chosen from phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl.

8. The compounds of formula (XI)

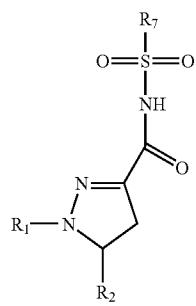

(XI)

wherein $R_1$ and $R_2$, which may be identical or different, are each chosen from phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl; and $R_7$ is chosen from benzyl, phenyl, thienyl and pyridyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$ dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms.

9. The compounds of formula (XII)

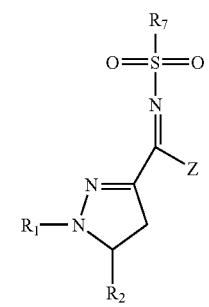

(XII)

wherein R₁ and R₂, which may be identical or different, are each chosen from phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl; and R₇ is chosen from benzyl, phenyl, thienyl and pyridyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$ dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms; and wherein Z is chosen from Cl and Br atoms.

10. A method for preparing a medicament, comprising: combining an effective amount of at least one compound of formula (1), a tautomer, a stereoisomer, or N-oxide thereof, or a salt or hydrate of any of the foregoing:

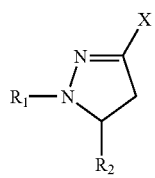

(I)

wherein:

R₁ and R₂, which may be identical or different, are each chosen from phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

X is chosen from (i) and (ii),

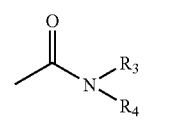

(i)

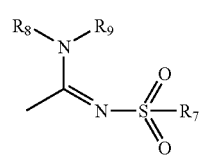

(ii)

wherein:

R₃ is chosen from hydrogen atoms and branched or linear $C_{1-3}$ alkyl groups;

R₄ is chosen from branched or linear $C_{1-8}$ alkyls and $C_{3-8}$-cycloalkyl-$C_{1-2}$-alkyl groups, branched or linear $C_{1-8}$ alkoxys, $C_{3-8}$ cycloalkyls, $C_{5-10}$ bicycloalkyls, $C_{6-10}$ tricycloalkyls, optionally comprising at least one heteroatom chosen from O, N, and S and optionally substituted with a group chosen from hydroxy groups, from 1 to 3 methyl groups, ethyl groups, and from 1 to 3 fluoro atoms, phenoxy, benzyl, phenethyl and phenylpropyl groups, optionally substituted on the phenyl ring with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, pyridyl and thienyl groups, and NR₅R₆ wherein:

R₅ and R₆, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms; or R₃ and R₄, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms;

R₇ is chosen from benzyl, phenyl, thienyl and pyridyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$ dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms;

$R_8$ is chosen from hydrogen atoms and branched or linear $C_{1-3}$ alkyls;

$R_9$ is chosen from hydrogen atoms and branched or linear $C_{1-8}$ alkyls, $C_{3-8}$ cycloalkyls and $C_{2-10}$ heteroalkyls, optionally substituted with a group chosen from keto groups, trifluoromethyl groups and fluoro atoms, amino, hydroxy, phenoxy and benzyloxy groups branched or linear $C_{1-8}$ alkoxy groups, optionally substituted with an entity chosen from hydroxy groups, trifluoromethyl groups and fluoro atoms, phenyl, benzyl, pyridyl, thienyl, pyridylmethyl and phenethyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S, and the heterocyclic group is optionally substituted with $C_{1-2}$ alkyl groups; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and $—SO_2—$ groups, wherein the heterocyclic group is optionally substituted with $C_{1-2}$ alkyls, hydroxys, phenyls, methylaminos, dimethylaminos, azetidinyls, pyrrolidinyls, piperidinyls and hexahydro-1H-azepinyls; and at least one pharmaceutically acceptable carrier, at least one pharmaceutically acceptable auxiliary substance, or a combination thereof.

11. The method of claim 10, wherein:

$R_1$ and $R_2$, which may be identical or different, are each chosen from phenyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

$R_3$ comprises a hydrogen atom;

$R_4$ is chosen from branched or linear $C_{1-8}$ alkyls, branched or linear $C_{1-8}$ alkoxys, and $C_{3-8}$ cycloalkyls, optionally substituted with at least one group chosen from hydroxy groups, from 1 to 3 methyl groups, an ethyl group, and from 1 to 3 fluoro atoms, phenoxy, -pyridyl and thienyl groups, and $NR_5R_6$ wherein:

$R_5$ and $R_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S; or $R_3$ and $R_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from methyl groups, hydroxy groups, trifluoromethyl groups and fluoro atoms;

$R_7$ is chosen from phenyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-10}$ cycloalkyls, and $C_{5-10}$ bicycloalkyls, naphthyl, amino groups, and $C_{1-8}$ dialkylamino groups, $C_{1-8}$ monoalkylamino groups and saturated or unsaturated, monocyclic or bicyclic, heterocyclic groups having from 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with branched or linear $C_{1-3}$ alkyls and hydroxys;

$R_8$ is chosen from hydrogen atoms and branched or linear $C_{1-3}$ alkyls;

$R_9$ is chosen from hydrogen atoms and branched or linear $C_{1-4}$ alkyls or $C_{3-8}$ cycloalkyls, optionally substituted with a group chosen from trifluoromethyl groups and fluoro atoms, amino, hydroxy, phenoxy and benzyloxy groups, branched or linear $C_{1-8}$ alkoxy groups, phenyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein R₁₀ and R₁₁, which may be identical or different, are each chosen from $C_{1-4}$ alkyls and $C_{2-4}$ trifluoroalkyls or R₁₀ and R₁₁, together with the nitrogen atom to which they are bonded, form a saturated or unsaturated heterocyclic group comprising from 4 to 8 ring atoms wherein the heterocyclic group comprises one or two atoms chosen from O, N, and S; or R₈ and R₉, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —SO₂— groups.

12. The method of claim 10, wherein the formula (1) compound is chosen from:

N-(piperidin-1-yl)-1-(4-chlorophenyl)-5-phenyl-4,5-dihydro-(1H)-pyrazole-3-carboxamide, N-(Piperidin-1-yl)-5-(4-chlorophenyl)-1-(2,4-dichlorophenyl)-4,5-dihydro-(1H)-pyrazole-3-carboxamide, N-(Piperidin-1-yl)-1-(2,4-dichlorophenyl)-5-phenyl-4,5-dihydro-(1H)-pyrazole-3-carboxamide, N-(Cyclohexyl)-1-(2,4-dichlorophenyl)-5-phenyl-4,5-dihydro-(1H)-pyrazole-3-carboxamide, N-[(4-fluorophenyl)sulfonyl]-1-(4-chlorophenyl)-5-phenyl-4,5-dihydro-(1H)-pyrazole-3-carboxamidine, N-[(4-fluorophenyl)sulfonyl]-1-(2,4-dichlorophenyl)-5-phenyl-4,5-dihydro-(1H)-pyrazole-3-carboxamidine, N-[(4-chlorophenyl)sulfonyl]-N'-methyl-1-(4-chlorophenyl)-5-phenyl-4,5-dihydro-(1H)-pyrazole-3-carboxamidine, N-[(4-Chlorophenyl)sulfonyl]-N'-methyl-1-(2,4-dichlorophenyl)-5-phenyl-4,5-dihydro-(1H)-pyrazole-3-carboxamidine, N-{[(4-Trifluoromethyl)phenyl]sulfonyl}-N'-methyl-1-(2,4-dichlorophenyl)-5-phenyl-4,5-dihydro-(1H)-pyrazole-3-carboxamidine, N-[(piperidin-1-yl)sulfonyl]-N'-methyl-1-(4-chlorophenyl)-5-phenyl-4,5-dihydro-(1H)-pyrazole-3-carboxamidine, and N-[(Morpholin-4-yl)sulfonyl]-N'-methyl-1-(2,4-dichlorophenyl)-5-phenyl-4,5-dihydro-(1H)-pyrazole-3-carboxamidine.

13. A method for treating eating disorders, obesity, juvenile obesity, and drug induced obesity in a patient in need thereof comprising:

administering an effective amount of at least one compound of formula (1), a tautomer, a stereoisomer, or an N-oxide thereof, or a salt or a hydrate of any of the foregoing:

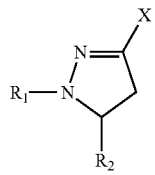

(I)

wherein:

R₁ and R₂, which may be identical or different, are each chosen from phenyls, thienyls and pyridyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

X is chosen from (i) and (ii),

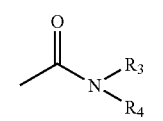

(i)

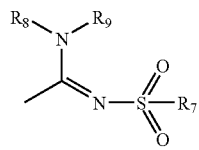

(ii)

wherein:

R₃ is chosen from hydrogen atoms and branched or linear $C_{1-3}$ alkyl groups;

R₄ is chosen from branched or linear $C_{1-8}$ alkyls and $C_{3-8}$-cycloalkyl-$C_{1-2}$-alkyl groups, branched or linear $C_{1-8}$ alkoxys, $C_{3-8}$ cycloalkyls, $C_{5-10}$ bicycloalkyls, $C_{6-10}$ tricycloalkyls, optionally comprising at least one heteroatom chosen from O, N, and S and optionally substituted with a group chosen from hydroxy groups, from 1 to 3 methyl groups, ethyl groups, and from 1 to 3 fluoro atoms, phenoxy, benzyl, phenethyl and phenylpropyl groups, optionally substituted on the phenyl ring with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, pyridyl and thienyl groups, and NR₅R₆ wherein:

R₅ and R₆, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms; or R₃ and R₄, together with the nitrogen atom to which they are attached, form a saturated or unsaturated, monocyclic or bicyclic heterocyclic group comprising from 4 to 10 ring atoms, wherein the heterocyclic group comprises one or two heteroatoms chosen from O, N, and S and wherein the heterocyclic group is optionally substituted with a group chosen from branched or linear $C_{1-3}$ alkyls, phenyls, hydroxy, trifluoromethyl groups and fluoro atoms R₇ is chosen from benzyl, phenyl, thienyl and pyridyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-8}$ alkenyls, $C_{3-10}$ cycloalkyls, $C_{5-10}$ bicycloalkyls, $C_{6-10}$ tricycloalkyls and $C_{5-8}$ cycloalkenyls, naphthyl, amino groups, and $C_{1-8}$dialkylamino groups, $C_{1-8}$ monoalkylamino groups and saturated or unsaturated, monocyclic or bicyclic, heterocyclic groups having 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with anentity chosen from branched or linear $C_{1-3}$ alkyls, phenyls, hydroxys, trifluoromethyls and fluoro atoms;

$R_8$ is chosen from hydrogen atoms and branched or linear $C_{1-3}$ alkyls;

$R_9$ is chosen from hydrogen atoms and branched or linear $C_{1-8}$ alkyls, $C_{3-8}$ cycloalkyls and $C_{2-10}$ heteroalkyls, optionally substituted with a group chosen from keto groups, trifluoromethyl groups and fluoro atoms, amino, hydroxy, phenoxy and benzyloxy groups branched or linear $C_{1-8}$ alkoxy groups, optionally substituted with an entity chosen from hydroxy groups, trifluoromethyl groups and fluoro atoms, phenyl, benzyl, pyridyl, thienyl, pyridylmethyl and phenethyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S, and the heterocyclic group is optionally substituted with $C_{1-2}$ alkyl groups; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —SO$_2$— groups, wherein the heterocyclic group is optionally substituted with $C_{1-2}$ alkyls, hydroxys, phenyls, methylaminos, dimethylaminos, azetidinyls, pyrrolidinyls, piperidinyls and hexahydro-1H-azepinyls.

14. The method according to claim 13, wherein:

$R_1$ and $R_2$, which may be identical or different, are each chosen from phenyls, optionally substituted with 1, 2 or 3 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and naphthyl;

$R_3$ comprises a hydrogen atom;

$R_4$ is chosen from branched or linear $C_{1-8}$ alkyls, branched or linear $C_{1-8}$ alkoxys, and $C_{3-8}$ cycloalkyls, optionally substituted with at least one group chosen from hydroxy groups, from 1 to 3 methyl groups, an ethyl group, and from 1 to 3 fluoro atoms, phenoxy, -pyridyl and thienyl groups, and $NR_5R_6$ wherein:

$R_5$ and $R_6$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S; or $R_3$ and $R_4$, together with the nitrogen atom to which they are attached, form a saturated or unsaturated, monocyclic or bicyclic, heterocyclic group comprising from 4 to 10 ring atoms, wherein the heterocyclic group comprises one or two heteroatoms chosen from O, N, and S and wherein the heterocyclic group is optionally substituted with a group chosen from methyl groups, hydroxy groups, trifluoromethyl groups and fluoro atoms;

$R_7$ is chosen from phenyl groups, optionally substituted on the aromatic ring with 1, 2, 3 or 4 substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, $C_{1-8}$ branched or linear alkyls, $C_{3-10}$ cycloalkyls, and $C_{5-10}$ bicycloalkyls, naphthyl, amino groups, and $C_{1-8}$ dialkylamino groups, $C_{1-8}$ monoalkylamino groups and saturated or unsaturated, monocyclic or bicyclic, heterocyclic groups having from 4 to 10 ring atoms, wherein the heterocyclic group comprises 1 or 2 nitrogen atoms and wherein the heterocyclic group optionally comprises 1 heteroatom chosen from O and S and wherein the heterocyclic group is optionally substituted with branched or linear $C_{1-3}$ alkyls and hydroxys;

$R_8$ is chosen from hydrogen atoms and branched or linear $C_{1-3}$ alkyls;

$R_9$ is chosen from hydrogen atoms and branched or linear $C_{1-4}$ alkyls or $C_{3-8}$ cycloalkyls, optionally substituted with a group chosen from trifluoromethyl groups and fluoro atoms, amino, hydroxy, phenoxy and benzyloxy groups, branched or linear $C_{1-8}$ alkoxy groups, phenyl groups wherein the aromatic rings are optionally substituted with 1, 2 or 3 of the substituents Y, which may be identical or different, chosen from branched or linear $C_{1-3}$-alkyls and alkoxys, phenyls, hydroxys, chloro, bromo, fluoro, iodo, trifluoromethyl, trifluoromethylthio, trifluoromethoxy, methylsulfonyl, carboxyl, trifluoromethylsulfonyl, cyano, carbamoyl, sulfamoyl and acetyl, and $NR_{10}R_{11}$ with the proviso when $R_8$ is chosen from a hydrogen atom or a methyl group, and wherein $R_{10}$ and $R_{11}$, which may be identical or different, are each chosen from $C_{1-4}$ alkyls and $C_{2-4}$ trifluoroalkyls or $R_{10}$ and $R_{11}$, together with the nitrogen atom to which they are bonded, form a saturated or unsaturated heterocyclic group comprising from 4 to 8 ring atoms wherein the heterocyclic group comprises one or two atoms chosen from O, N, and S; or $R_8$ and $R_9$, together with the nitrogen atom to which they are bonded, form a saturated or unsaturated, monocyclic or bicyclic heterocyclic group comprising from 4 to 10 ring atoms, wherein the heterocyclic group comprises one or two atoms chosen from O, N, and S, keto groups and —$SO_2$— groups.

15. The method according to claim 13, wherein the formula (1) compound is chosen from N-(piperidin-1-yl)-1-(4-chlorophenyl)-5-phenyl-4,5-dihydro-(1H)-pyrazole-3-carboxamide, N-(Piperidin-1-yl)-5-(4-chlorophenyl)-1-(2,4-dichlorophenyl)-4,5-dihydro-(1H)-pyrazole-3-carboxamide, N-(Piperidin-1-yl)-1-(2,4-dichlorophenyl)-5-phenyl-4,5-dihydro-(1H)-pyrazole-3-carboxamide, N-(Cyclohexyl)-1-(2,4-dichlorophenyl)-5-phenyl-4,5-dihydro-(1H)-pyrazole-3-carboxamide, N-[(4-fluorophenyl)sulfonyl]-1-(4-chlorophenyl)-5-phenyl-4,5-dihydro-(1H)-pyrazole-3-carboxamidine, N-[(4-fluorophenyl)sulfonyl]-1-(2,4-dichlorophenyl)-5-phenyl-4,5-dihydro-(1H)-pyrazole-3-carboxamidine, N-[(4-chlorophenyl)sulfonyl]-N'-methyl-1-(4-chlorophenyl)-5-phenyl-4,5-dihydro-(1H)-pyrazole-3-carboxamidine, N-[(4-Chlorophenyl)sulfonyl]-N'-methyl-1-(2,4-dichlorophenyl)-5-phenyl-4,5-dihydro-(1H)-pyrazole-3-carboxamidine, N-{[(4-Trifluoromethyl)phenyl]suifonyl}-N'-methyl-1-(2,4-dichlorophenyl)-5-phenyl-4,5-dihydro-(1H)-pyrazole-3-carboxamidine, N-[(piperidin-1-yl)sulfonyl]-N'-methyl-1-(4-chlorophenyl)-5-phenyl-4,5-dihydro-(1H)-pyrazole-3-carboxamidine, and N-[(Morpholin-4-yl)sulfonyl]-N'-methyl-1-(2,4-dichlorophenyl)-5-phenyl-4,5-dihydro-(1H)-pyrazole-3-carboxamidine.

16. The method according to claim 13, further comprising administering at least one lipase inhibitor.

17. The method according to claim 16, wherein the at least one lipase inhibitor is chosen from orlistat and lipstatin.

* * * * *

UNITED STATES PATENT AND TRADEMARK OFFICE
CERTIFICATE OF CORRECTION

| | | |
|---|---|---|
| PATENT NO. | : 7,745,476 B1 | Page 1 of 1 |
| APPLICATION NO. | : 11/033683 | |
| DATED | : June 29, 2010 | |
| INVENTOR(S) | : Lange et al. | |

It is certified that error appears in the above-identified patent and that said Letters Patent is hereby corrected as shown below:

\*Claim 1, col. 21, line 11, "1heteroatom" should read --1 heteroatom--.

Claim 1, col. 21, line 13, "anentity" should read --an entity--.

\*Claim 4, col. 25, line 14, "1heteroatom" should read --1 heteroatom--.

Claim 4, col. 25, line 16, "anentity" should read --an entity--.

Claim 9, col. 29, line 35, "anentity" should read --an entity--.

Claim 10, col. 31, line 13, "anentity" should read --an entity--.

Signed and Sealed this

Twenty-first Day of September, 2010

David J. Kappos
*Director of the United States Patent and Trademark Office*